(12) United States Patent
Falco et al.

(10) Patent No.: US 7,176,353 B2
(45) Date of Patent: Feb. 13, 2007

(54) GENES ENCODING SULFATE ASSIMILATION PROTEINS

(75) Inventors: Saverio Carl Falco, Arden, DE (US); Stephen M. Allen, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 354 days.

(21) Appl. No.: 10/731,525

(22) Filed: Dec. 9, 2003

(65) Prior Publication Data

US 2004/0121440 A1 Jun. 24, 2004

Related U.S. Application Data

(62) Division of application No. 09/720,318, filed as application No. PCT/US99/15808 on Jul. 13, 1999, now Pat. No. 6,730,827.

(60) Provisional application No. 60/092,833, filed on Jul. 14, 1998.

(51) Int. Cl.
*A01H 5/00* (2006.01)
*C12N 9/02* (2006.01)
*C12N 5/02* (2006.01)
*C07H 21/04* (2006.01)

(52) U.S. Cl. .................. 800/295; 800/298; 435/189; 435/410; 435/252.3; 435/252.33; 435/468; 435/471; 435/320.1; 536/23.1; 536/23.2

(58) Field of Classification Search .................... None
See application file for complete search history.

(56) References Cited

OTHER PUBLICATIONS

EMBL Sequence Library Data Accession No. D89631, Jul. 30, 1997, Sohlberg, L.E. et al., Nucleotide Sequence of a cDNA encoding a Cys proteinase from germinating bean cotyledons, XP-002129910.
EMBL Sequnce Library Data Accession No. O49307, Jun, 1, 1998, Federspiel, N.A. et al., XP-002129911.
EMBL Sequence Library Data Accession No. D25000, Nov. 30, 1993, Minobe, Y. et al., Rice cDNA from root, XP-002129912.
Frank W. Smith et al., PNAS, vol. 92:9373-9377, Sep. 1995, Plant members of a family of sulfate transporters reveal functional subtypes, XP-002129913.
Hideki Takahashi et al., Plant & Cell Phys., vol. 39 suppl, pp. S148, 1998, Antisense repression of sulfate transporter in transgenic *Arabidopsis thaliana* plants, XP-002121793.
Hideki Takahashi et al., PNAS, vol. 94:11102-11197, Sep. 1997, Regulation of sulfur assimilation in higher plants: A sulfate trnasporter induced in sulfate-starved roots plays a central role in *Arabidopsis thaliana*.
EMBL Sequence Library Data Accession No. X96761, Mar. 25, 1997, NG, A. et al., Isolation & characterization of a lowly expressed cDNA from the resurrection grass *Sporobolus stapfianus* with homology to eukaryote sulfate transporter proteins, XP-002121791.
EMBL Sequence Library Data Accession No. AF016306, Jan. 8, 1998, Bolchi, A. et al., Coordinate modulation of maize sulfate permease and ATP sulfate permease and ATP sulfurylase mRNAs in response to variations in sulfur nutritional status: stereospecific down-regulation by L-cysteine, XP-002121790.
EMBL Sequence Data Library Accession No. O48889, Jun. 1, 1998, Bolchi, A. et al.
Frank W. Smith et al., The Plant Journal, vol. 12(4):875-884, 1997, Regulation of expression of a cDNA from barley roots encoding a high affinity sulphate transporter, XP-002129909.
Antje Prior et al., Biochimica et Biophysica Acta, vol. 1430:25-38, 1999, Structural and kinetic properties of adenylyl sulfate reductase from *Catharanthus roseus* cell cultures.
Senta Heiss et al., Plant Mol. Biol., vol. 39:847-857, 1999, Cloning sulfur assimilation genes of *Brassica juncea* L.: *cadmium* differentially affects the expression of a putative low-affinity sulfate transporter and isoforms of ATP sulfurylase and APS reductase.
John L. Wray et al., Chemico-Biological Interactions, vol. 109:153-167, 1998, Redefining reductive sulfate assimilation in higher plants: a role for APS reductase, a new member of the *thioredoxin* superfamily?
Julie Ann Bick et al., Current Opinion in Plant Biology, 1998, pp. 240-244, Plant sulfur metabolism—the reduction of sulfate to sulfite.
Julie-Ann Bick et al., PNAS, vol. 95:8404-8409, Jul. 1998, Glutareodxin function for the carboxyl-terminal domain of the plant-type 5'-adenylylsulfate reductase.
Jose F. Gutierrez-Marcos et al., PNAS, vol. 93:13377-13382, 1996, Three members of a novel small gene-family from *Arabidopsis thaliana* able to complement funtionally an *Escherichia coli* mutant defective in PAPS reductase activity encode proteins with a thioredoxin-like domain and "APS reductase" activity.

(Continued)

*Primary Examiner*—Nashaat T. Nashed

(57) ABSTRACT

This invention relates to an isolated nucleic acid fragment encoding a sulfate assimilation protein. The invention also relates to the construction of a chimeric gene encoding all or a portion of the sulfate assimilation protein, in sense or antisense orientation, wherein expression of the chimeric gene results in production of altered levels of the sulfate assimilation protein in a transformed host cell.

11 Claims, 3 Drawing Sheets

OTHER PUBLICATIONS

Amit Setya et al., PNAS, vol. 93:13383-13388, 1996, Sulfate reduction in higher plants: Molecular evidence for a novel 5'-adenylylsulfate reductase.
EMBL Sequence Library Data Accession No. C27405, Aug. 6, 1997, Sasaki, T. et al., Rice cDNA from *callus*, XP-002121812.
EMBL Sequence Library Data Accession No. AF071890, Jun. 29, 1998, Mbeguie-A-Mbeguie D. et al., Molecular cloning and partial nucleotide sequence of a sulfite reductase from apricot fruit, XP-002128211.
EMBL Sequence Library Data Accession No. D50679, Dec. 1, 1997, Ideguchi, T. et al., cDNA cloning and functional expression of ferredoxin-dependent sulfite reductase from miaze in *E. coli* cells, XP-002128212.
Christine Bork et al., Gene, vol. 212:147-153, 1998, Isolation and characterization of a gene for assimiliatory sulfite reductase from *Arabidopsis thaliana*.
Andreas Bruhl et al., Biochimia et Biophysica Acta, vol. 1295:119-124, 1996, A cDNA clone from *Arabidopsis thaliana* encoding plastidic ferredoxin: sulfite reductase.
Database WPI, Derwent Publ., Ltd., JP-62 455773, Mitsubishi Corp., Sep. 6, 1994, XP-002121814.
EMBL Sequence Library Data Accession No. AU068082, Jun. 7, 1999, Sasaki, T. et al., Rice cDNA from *callus*, XP-002128630.
EMBL Sequence Library Data Accession No. AQ688702, Jul. 2, 1999, Yu, Y. et al., A BAC Encd sequencing framework to sequence the rice genome, XP-002128631.
Saito, K., Stress Responses of Photosynthetic organisms, 1998, pp. 215-226, Molecular Aspects of Sulfur Assimilation and Acclimiation to Sulfur Supply in Plants.
Kazuki Saito et al., Plant Phys., vol. 106:887-895. 1994, Moedulation of Cystine Biosynthesis in Chloroplasts of Transgenic Tobacco Overexpressing Cystein Synthase [O-Acetylserine(thiol)-lyase]1.
Kazuki Saito et al., Comptes REndu De L'Academie Des Sciences, vol. 319:969-973, 1996, Molecular characterization of cysteine biosynthetic enzymes in plants.
Yoo, B. et al., Plant Phys. suppl., vol. 114:267, 1997, Regulation of recombinant soybean serine acetyltransferase by CDPK.
EMBL Sequence Library Data Accession No. p93544, May 1, 1997, Saito, K. et al., XP-002128628.
EMBL Sequence Library Data Accession No. C26373, Aug. 6, 1997, Sasaki, T. Rice cDNa from *callus*, XP-002128627.
Michael A. Roberts et al., Plant Molecular biology, vol. 30:1041-1049, 1996, Cloning and characterisation of an *Arabidopsis thaliana* cDNa clone encoding an organellar isoform of serine acetyltransferase.

Kazuki Saito et al., Journ. of Biol. Chem., vol. 270(27):16321-16326, 1995, Molecular cloning and characterization of a Plant Serine acetyltransferase playing a regulatory role in cystein biosynthesis from watermelon.
EMBL Sequence Data Library Accession No. AI637166, Apr. 27, 1999, Walbot, V., Maize ESTs from various cDNA libraries sequenced at Stanford University, XP-002123195.
Sangman Lee et al., Biochem. and Biophys. Res. Comm., vol. 247:171-175, 1998, APS Kinase from *Arabidopsis thaliana*: Genomic Organization, Expression, and Kintetic Analysis of the Recombinant Enzyme.
Ajay Jain et al., Plant Phys., vol. 105:771-772, 1994, A cDNA clone for 5'-Adenylylphosphosulfate Kinase from *Arabidopsis thaliana*.
Sandra Schiffmann et al., FEBS Lett., vol. 355:229-232, 1994, APS-sulfotransferase activity is identical to higher plant APS-kinase.
Hildegard E. Arz et al., Biochimica et Biophysica Acta., vol. 1218:447-452, 1994, A cDNA for adenylyl sulphate (APS)-kinase from *Arabidopsis thaliana*.
Angelo Bolchi et al., Plant Mol. Biol., vol. 39:527-537, 1999, Coordinate modulation of maize sulfate permease and ATP sulfurylase mRNAs in response to variationos in sulfur nutritional status: stereospecific down-regulation by L-cystein.
Keiko Yonekura-Sakakibara et al., J. Biochem., vol. 24:615-621, 1998, Molecular Characterization of Tobacco Sulfite Reductase: Enzyme Purification, Gene Cloning, and Gene Expression Analysis.
Yichang Chen et al., Plant phys., vol. 116:867-869, 1998, Three Genomic Clones from *Arabidopsis thaliana* Encoding 5'-Adenylsulfate Reductase.
GENBANK Database Accession No. AAC26979, NCBI GI No. 2738756, 5'-adenylylsulfate reducatase [*Arabidopsis thaliana*], Jul. 21, 1998.
GENBANK Database Accession No. AAB05871, NCBI GI No. 1488043, PAPS-reductase-like protein [*Catharanthus roseus*], Aug. 10, 1996.
GENBANK Database Accession No. AAB05871.1, NCBI GI No. 1488043, PAPS-reductase-like protein [*Catharanthus roseus*], Nov. 2, 1999.
GENBANK Database Accession No. AAB05871.2, NCBI GI No. 12831474, PAPS-reductase-like protein [*Catharanthus roseus*], Feb. 15, 2001.

Figure 1A

```
                        1                                                           60
SEQ ID NO:2    ------------------------------------------------------------
SEQ ID NO:4    ------------------------------------------------------------
SEQ ID NO:6    MALAVSTTSSSAAAAAASSFFSRLGSSSDAKAPQIGSFRFPERPQVSSGVVNLTQ-----
SEQ ID NO:8    MALAFTSSIS------APTSTF--------PSSEPKLPQIGSIRISERPIGGAVNFNLSQ-
SEQ ID NO:10   MASATASISSHSIALR--------------------DLKAARIGAVR--QQVAVVPAGLPATAPK
SEQ ID NO:11   MALAFTSST---AIHGSLSSSF-----EQTKAAAAQFGSFQPLDRPHTISPSVNVSR--
SEQ ID NO:12   MAMSVNVSSSSSGIINS-------RFGVSLEPKVSQIGSLRLLDRVHVAPVSLNLSG--

61                                                          120
SEQ ID NO:2    ------------------------------------------------------------
SEQ ID NO:4    ------------------------------------------------------------
SEQ ID NO:6    -RRSS-VRPL-NAEPQRNDSVVPLAAT-I--VAPEVEK-EKEDFEQLAKDLENSSPLEIM
SEQ ID NO:8    -RRSL-VKPV-NAEPPRKDSIVPLAATTI--VASASET-KEEDFEQIASDLDNASPLEIM
SEQ ID NO:10   GQRARAVRPLCAAEPARKPVSASAASSPVAPVEEEASAVAAVDYEALAQELVGASPLEIM
SEQ ID NO:11   -RRLA-VKPI-NAEPKRNESIVPSAATTV--APEVEEKVDVEDYEKLADELQNASPLEIM
SEQ ID NO:12   -KRSSSVKPL-NAEPKTKDSMIPLAATMVAEIAEEVVEIEDFEELAKKLENASPLEIM 121                                                         180
SEQ ID NO:2    ------------------------------------------------------------
SEQ ID NO:4    ------------------------------------------------------------
SEQ ID NO:6    DKALEKFGNDIAIAFSGAEDVALIEYAHLTGRPYRVFSLDTGRLNPETYKFFDAVEKHYG
SEQ ID NO:8    DRALDKFGNDIAIAFSGAEDVALIEYAKLTGRPFRVFSLDTGRLNPETYQLFDAVEKHYG
SEQ ID NO:10   DRALDMFGSEIAIAFSGAEDVALIEYAKLTGRPFRVFSLDTGRLNPETYELFDKVEKHYG
SEQ ID NO:11   DKSLAKFGNDIAIAFSGAEDVALIEYAHLTGRPFRVFSLDTGRLNPETYKFFDTVEKQYG
SEQ ID NO:12   DKALEKYGNDIAIAFSGAEDVALIEYAHLTGRPFRVFSLDTGRLNPETYRFFDAVEKHYG
```

Figure 1B

```
         181                                                            240
SEQ ID NO:2   ------FPDASEVQELVRTKGLFSFYEDGHQECCRVRKVRPLRRALKGLRAWITGQRKDQ
SEQ ID NO:4   --TRYMFPDAIVVQGLVRTKGLFSFYEDGHQECCRVRKVRPLRRALKGLRAWITGQRKDQ
SEQ ID NO:6   IHIEYMFPDAVEVQALVRTKGLFSFYEDGHQECCRVRKVRPLRRALKGLKAWITGQRKDQ
SEQ ID NO:8   IRIEYMFPDAVEVQALVRSKGLFSFYEDGHQECCRVRKVRPLRRALKGLRAWITGQRKDQ
SEQ ID NO:10  IHIEYMFPEASEVQDLVRSKGLFSFYEDGHQECCRVRKVRPLRRALKGLRAWITGQRKDQ
SEQ ID NO:11  IHIEYMFPDAVEVQALVRSKGLFSFYEDGHQECCRVRKVRPLRRALKGLKAWITGQRKDQ
SEQ ID NO:12  IRIEYMFPDSVEVQGLVRSKGLFSFYEDGHQECCRVRKVRPLRRALKGLKAWITGQRKDQ 241                                                            300
SEQ ID NO:2   SPGTRASIPIVQVDPSFEGLDGGAGSLVKWNPVANVXGKDIWTFLRTMDVPVNTLHAQGY
SEQ ID NO:4   SPGTRSEIPVVQVDPSFEGLVGGEGSLVKWNPVANVDGRDVWNFLRAMNVPVNALHSQGY
SEQ ID NO:6   SPGTRSEIPIVQVDPVFEGLDGGIGSLVKWNPVANVNGLDIWNFLRTMNVPVNSLHSQGY
SEQ ID NO:8   SPGTRSEIPVVQVDPAFEGMDGGIGSLVKWNPVANVKGHDIWNFLRTMNVPVNSLHAKGY
SEQ ID NO:10  SPGTRASIPVVQVDPSFEGLDGGAGSLIKWNPVANVDGKDIWTFLRTMDVPVNTLHAQGY
SEQ ID NO:11  SPGTRSEIPVVQVDPVFEGMDGGVGSLVKWNPVANVEGKDIWNFLRAMDVPVNTLHSQGY
SEQ ID NO:12  SPGTRSEIPVVQVDPVFEGLDGGVGSLVKWNPVANVEGNDVWNFLRTMDVPVNTLHAAGY 301                                                            360
SEQ ID NO:2   VSIGCEPCTRPVLPGQHEREGRWWWEDAKAKECGLHKGNIDKDAQAA-----APRSANGN
SEQ ID NO:4   VSIGCEPCTRPVLPGQHEREGRWWWEDAKAKECGLHKGNIDKDAQAA------APRSANGN
SEQ ID NO:6   VSIGCEPCTRPVLPGQHEREGRWWWEDAKAKECGLHKGNIKDAN-----GNGVAQAEGGE
SEQ ID NO:8   VSIGCEPCTRPVLPGQHEREGRWWWEDAAAKECGLHKGNLKQEDAAQLNGNGTSQGNGSA
SEQ ID NO:10  VSIGCEPCTRPVLPGQHEREGRWWWEDAKAKECGLHKGNVKQQKEEDVNGNGLSQSHANG
SEQ ID NO:11  VSIGCEPCTRPVLPGQHEREGRWCWEDAKAKECGLHNGNIDKEGQAPK----VGVNGNGS
SEQ ID NO:12  VSIGCEPCTRPVLPGQHEREGRWWWEDATAKECGLHKGDIKEGT----LIIWDGAVNGN
SEQ ID NO:?   ISIGCEPCTKAVLPGQHEREGRWWWEDAKAKECGLHKGNVKENSDD-------AKVNGE
```

Figure 1C

```
              361                                                           420
SEQ ID NO:2   GSAGAPDIFESPAVVSLTRTGIENLLRLENRAEPWLVVLYAPWCPFCQAMEASYVELAEK
SEQ ID NO:4   GTVTDADIFESKNVVTLSRSGIENLSKLQERKEPWIVVLYAPWCQFCQGMEKSYLELAEK
SEQ ID NO:6   ---TVADIFISQNVVSLSRSGIENLAKLENRKEHWLVVLYAPWCRFCQAMEESYVDLAEK
SEQ ID NO:8   DATTVPDIFNSPNVVNLSRTGIENLAKLEDRKEPWLVVLYAPWCPYCQAMEESYVDLADK
SEQ ID NO:10  AEASAPDIFQSQAIVNLTRPGIENLLRLENRAEPWLTVLYAPWCPYCQAMEASYVELAEK
SEQ ID NO:11  GSDTIADIFDTNNVTSLSRPGIENLLKLEERREAWLVVLYAPWCRFCQAMEGSYLELAEK
SEQ ID NO:12  SKSAVADIFKSENLVTLSRQGIENLMKLENRKEPWIVVLYAPWCPFCQAMEASYDELADK 421                                                           480
SEQ ID NO:2   LA--GSGVKVAKFRADGEQKPFAQAELQLQSFPTVLLFPGRTARP-IKYPSEKRDVDSLL
SEQ ID NO:4   LAVSGGGVKVGKFRADGAEKEFAHQELQLGSFPTILFFPKHSSKA-IKYPSEKRDVESLL
SEQ ID NO:6   LA--RSGVKVAKFRADGEQKEYAKSELQLGSFPTILLFPKHSSQP-IKYPSEKRDVDSLT
SEQ ID NO:8   LA--GSTGMKVGKFRADGEQKEFAKSELQLGSFPTILFFPKHSSRPTIKYPSEKRDVDSLM
SEQ ID NO:10  LS--GSGIKVAKFRADGEQKPFAQAELQLGSFPTILLFPGRTVKP-IKYPSEKRDVQSLL
SEQ ID NO:11  LA--GSGVKVGKFKADGDQKAFAQQELQLNSSPTILFFPKHSSKP-IKYPSEKRDVDSLM
SEQ ID NO:12  LA--GSGIKVAKFRADGDQKEFAKQELQLGSFPTILVFPKNSSRP-IKYPSEKRDVESLT 481  487
SEQ ID NO:2   AFVNSLR
SEQ ID NO:4   AFVNALR
SEQ ID NO:6   AFVNALR
SEQ ID NO:8   AFVNALR
SEQ ID NO:10  AFVNSLR
SEQ ID NO:11  AFVNALR
SEQ ID NO:12  SFLNLVR
```

GENES ENCODING SULFATE ASSIMILATION PROTEINS

This application is a divisional of U.S. application Ser. No. 09/720,318, filed Dec. 21, 2000, now U.S. Pat. No. 6,730,827, issued May 4, 2004, which is a National Stage Application of PCT/US99/15808, filed Jul. 13, 1999, which claims the benefit of U.S. Provisional Application No. 60/092,833, filed Jul. 14, 1998.

FIELD OF THE INVENTION

This invention is in the field of plant molecular biology. More specifically, this invention pertains to nucleic acid fragments encoding sulfate assimilation proteins in plants and seeds.

BACKGROUND OF THE INVENTION

Sulfate assimilation is the process by which environmental sulfur is fixed into organic sulfur for use in cellular metabolism. The two major end products of this process are the essential amino acids cysteine and methionine. These amino acids are limiting in food and feed; they cannot be synthesized by animals and thus must be acquired from plant sources. Increasing the level of these amino acids in feed products is thus of major economic value. Key to that process is increasing the level of organic sulfur available for cysteine and methionine biosynthesis.

Multiple enzymes are involved in sulfur assimilation. These include: High affinity sulfate transporter and low affinity sulfate transporter proteins which serve to transport sulfur from the outside environment across the cell membrane into the cell (Smith et al. (1995) *PNAS* 92(20): 9373–9377). Once sulfur is in the cell sulfate adenylyltransferase (ATP sulfurylase) (Bolchia et al. (1999) *Plant Mol. Biol.* 39(3):527–537) catalyzes the first step in assimilation, converting the inorganic sulfur into an organic form, adenosine-5' phosphosulfate (APS). Next, several enzymes further modify organic sulfur for use in the biosynthesis of cysteine and methionine. For example, adenylylsulfate kinase (APS kinase), catalyzes the conversion of APS to the biosynthetic intermediate PAPS (3'-phosphoadenosine-5' phosphosulfate) (Arz et al. (1994) *Biochim. Biophy. Acta* 1218(3): 447–452). APS reductase (5' adenylyl phosphosulphate reductase) is utilized in an alternative pathway, resulting in an inorganic but cellularly bound (bound to a carrier), form of sulfur (sulfite) (Setya et al. (1996) *PNAS* 93(23):13383–13388). Sulfite reductase further reduces the sulfite, still attached to the carrier, to sulfide and serine O-acetyltransferase converts serine to O-acetylserine, which will serve as the backbone to which the sulfide will be transferred to from the carrier to form cysteine (Yonelcura-Sakakibara et al. (1998) *J. Biolchem.* 124(3):615–621 and Saito et al. (1995) *J. Biol. Chem.* 270(27):16321–16326).

As described, each of these enzymes is involved in sulfate assimilation and the pathway leading to cysteine biosynthesis, which in turn serves as an organic sulfur donor for multiple other pathways in the cell, including methionine biosynthesis. Together or singly these enzymes and the genes that encode them have utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

SUMMARY OF THE INVENTION

The instant invention relates to isolated nucleic acid fragments encoding sulfate assimilation proteins. Specifically, this invention concerns an isolated nucleic acid fragment encoding an APS reductase and an isolated nucleic acid fragment that is substantially similar to an isolated nucleic acid fragment encoding an APS reductase. In addition, this invention relates to a nucleic acid fragment that is complementary to the nucleic acid fragment encoding APS reductase. An additional embodiment of the instant invention pertains to a polypeptide encoding all or a substantial portion of an APS reductase.

In another embodiment, the instant invention relates to a chimeric gene encoding an APS reductase, or to a chimeric gene that comprises a nucleic acid fragment that is complementary to a nucleic acid fragment encoding an APS reductase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an APS reductase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an APS reductase in a transformed host cell comprising: a) transforming a host cell with a chimeric gene comprising a nucleic acid fragment encoding an APS reductase; and b) growing the transformed host cell under conditions that are suitable for expression of the chimeric gene wherein expression of the chimeric gene results in production of altered levels of APS reductase in the transformed host cell.

An addition embodiment of the instant invention concerns a method for obtaining a nucleic acid fragment encoding all or a substantial portion of an amino acid sequence encoding an APS reductase.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A–1C show a comparison of the amino acid sequences set forth in SEQ ID NOs:2, 4, 6, 8 and 10 and the *Catharanthus roseus* and *Arabidopsis thaliana* sequences (SEQ ID NOs:11 and 12 respectively).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Sulfate Assimilation Proteins

| Protein | Clone Designation | SEQ ID NO: | |
|---|---|---|---|
| | | (Nucleotide) | (Amino Acid) |
| APS reductase | Contig composed of: chp2.pk0008.e7 p0014.ctusu54rb | 1 | 2 |
| APS reductase | ids.pk0004.f12 | 3 | 4 |
| APS reductase | se4.11g09 | 5 | 6 |
| APS reductase | sl2.pk0064.g4 | 7 | 8 |
| APS reductase | wle1.pk0005.d6 | 9 | 10 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol*. 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of a sulfate assimilation protein have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other APS reductase enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of APS reductase in those cells. This enzyme is involved in sulfate assimilation and the pathway leading to cysteine biosynthesis, which in turn serves as an organic sulfur donor for multiple other pathways in the cell, including methionine biosynthesis. This enzyme and the gene(s) that encodes the protein has utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can. screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sulfate assimilation protein. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, impatiens, soybean and wheat tissues were prepared. The characteristics of the libraries are described below.

TABLE 2 cDNA Libraries from Corn, Impatiens, Soybean and Wheat

| Library | Tissue | Clone |
|---|---|---|
| chp2 | Corn (*Zea mays* L.) 11 day old leaf treated (24 hrs) with herbicides (A and B)* | chp2.pk0008.e7 |
| ids | *Impatiens balsamina* developing seed | ids.pk0004.f12 |
| p0014 | Corn (*Zea mays* L.) leaf: plant 3 ft tall, leaf 7 and leaf 8 | p0014.ctusu54rb |
| se4 | Soybean (*Glycine max* L.) embryo, 19 days after flowering | se4.11g09 |
| sl2 | Soybean (*Glycine max* L.) two week old developing seedlings treated with 2.5 ppm chlorimuron** | sl2.pk0064.g4 |
| wle1 | Wheat (*Triticum aestivum* L.) leaf 7 day old etiolated seedling | wle1.pk0005.d6 |

*herbicide descriptions:
A: Application of 2-[(2,4-dihydro-2,6,9-trimethyl[1]benzothiopyrano[4,3-c]pyrazol-8-yl)carbonyl]-1,3-cyclohexanedione S,S-dioxide; synthesis and methods of using this compound are described in WO 97/19087, incorporated herein by reference.
B: Application of 2-[(2,3-dihydro-5,8-dimethylspiro[4H-1-benzothiopyran-4,2'-[1,3]dioxolan]-6-yl)carbonyl]-1,3-cyclohexanedione S,S-dioxide; also named 2-[(2,3-dihydro-5,8-dimethylspiro[4H-1-benzothiopyran-4,2'-[1,3]dioxolan]-6-yl)carbonyl]-3-hydroxy-2-cyclohexen-1-one S,S-dioxide; synthesis and methods of using this compound are described in WO 97/01550, incorporated herein by reference
**Chlorimuron is commerically available from Sigma Chemical Co.

cDNA libraries may be prepared by any one of many methods available. For example, the cDNAs may be introduced into plasmid vectors by first preparing the cDNA libraries in Uni-ZAP*XR vectors according to the manufacturer's protocol (Stratagene Cloning Systems, La Jolla, Calif.). The Uni-ZAP*XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding sulfate assimilation proteins were identified by conducting BLAST (Basic Local Alignment Search Tool; Altschul et al. (1993) *J. Mol. Biol.* 215: 403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding APS Reductase

The BLASTX search using the EST sequences from clones listed in Table 3 revealed similarity of the polypeptides encoded by the cDNAs to APS reductase from *Catharanthus roseus* (NCBI Identifier No. gi 1488043) and *Arabidopsis thaliana* (NCBI Identifier No. gi 2738756). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Catharanthus roseus* and *Arabidopsis thaliana* APS Reductase

| Clone | Status | BLAST pLog Score |
|---|---|---|
| Contig composed of: chp2.pk0008.e7 p0014.ctusu54rb | Contig | 163.00 (gi 1488043) |
| ids.pk0004.f12 | FIS | 139.00 (gi 1488043) |
| se4.11g09 | FIS | >254.00 (gi 1488043) |
| sl2.pk0064.g4 | FIS | >254.00 (gi 2738756) |
| wle1.pk0005.d6 | FIS | >254.00 (gi 2738756) |

FIGS. 1A–1C present an alignment of the amino acid sequences set forth in SEQ ID NOs:2, 4, 6, 8 and 10 and the *Catharanthus roseus* and *Arabidopsis thaliana* sequences (SEQ ID NOs:11 and 12 respectively). The data in Table 4 represents a calculation of the percent identity of the amino acid sequences set forth in SEQ ID NOs:2, 4, 6, 8 and 10 and the *Catharanthus roseus* and *Arabidopsis thaliana* sequences (SEQ ID NOs:11 and 12).

TABLE 4

Percent Identity of Amino Acid Sequences Deduced From the Nucleotide Sequences of cDNA Clones Encoding Polypeptides Homologous to *Catharanthus roseus* and *Arabidopsis thaliana* APS Reductase

| SEQ ID NO. | Percent Identity to |
|---|---|
| 2 | 79% (gi 1488043) |
| 4 | 79% (gi 1488043) |
| 6 | 75% (gi 1488043) |
| 8 | 71% (gi 2738756) |
| 10 | 66% (gi 2738756) |

Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an APS reductase. These sequences represent the first corn, impatiens, soybean and wheat sequences encoding APS reductase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having adenosine 5'-phosphosulfate reductase activity, wherein the polypeptide has an amino acid sequence of at least 95% sequence identity, based on a Clustal method of alignment, when compared to SEQ ID NO:8, or
   (b) a full-length complement of the nucleotide sequence of (a).

2. The polynucleotide of claim 1, wherein the amino acid sequence of the polypeptide comprises SEQ ID NO:8.

3. The polynucleotide of claim 1, wherein the nucleotide sequence comprises SEQ ID NO:7.

4. A vector comprising the polynucleotide of claim 1.

5. A recombinant DNA construct comprising the polynucleotide of claim 1 operably linked to at least one regulatory sequence.

6. A method for transforming a cell, comprising introducing into a cell the recombinant DNA construct of claim 5.

7. A cell comprising the recombinant DNA construct of claim 5.

8. A method for the production of a polypeptide having adenosine 5'-phosphosulfate reductase activity comprising the steps of cultivating the cell of claim 7 under conditions that allow for the synthesis of the polypeptide and isolating the polypeptide from the cultivated cells, from culture medium, or from both the cultivated cells and the culture medium.

9. A method for producing a tranagenic plant comprising transforming a plant cell with the recombinant DNA construct of claim 5 regenerating a plant from the transformed plant cell.

10. A plant comprising the recombinant DNA construct of claim 5.

11. A seed comprising the recombinant DNA construct of claim 5.

* * * * *

SEQUENCE LISTING

```
<160> NUMBER OF SEQ ID NOS: 12

<210> SEQ ID NO 1
<211> LENGTH: 1215
<212> TYPE: DNA
<213> ORGANISM: Zea mays
<220> FEATURE:
<221> NAME/KEY: unsure
<222> LOCATION: (273)
<223> OTHER INFORMATION: n = a, c, g or t

<400> SEQUENCE: 1
tgttcccgga cgcgagcgag gtgcaggagc tggtgcgcac caagggcctc ttctccttct      60
acgaggacgg ccaccaggag tgctgccggg tgcgcaaggt gcggcccctg cgcagggcgc     120 tcaagggggct tagggcatgg atcaccggcc agaggaaaga ccagtccccc ggcaccaggg     180
ccagcatccc cattgtccag gttgatcctt ccttcgaagg cctggatggc ggggccggta     240
gcttggtcaa gtggaacccc gtggccaacg tcnacggcaa ggacatctgg actttcctgc     300
ggaccatgga cgtacctgtc aacaccctgc atgctcaggg ctacgtgtcc atcgggtgcg     360
agccgtgcac caggcccgtc ctgccggggc agcacgagcg tgaaggccgg tggtggtggg     420
aggacgccaa ggccaaggag tgcggcctcc acaagggcaa cattgacaag gacgcccagg     480
cggcggcccc caggtccgcc aacggcaacg gctcggcggg cgccccggac atcttcgaga     540
gccccgccgt ggtgtccctc acccgcaccg ggatcgagaa cctgctgcgc ctggagaacc     600
gcgccgagcc gtggctcgtg gtgctgtacg cgccctggtg cccgttctgc caggccatgg     660
aggcctccta cgtggagctg gccgagaagc tggcggggtc cggggtgaag gtggccaagt     720
```

-continued

```
tccgcgcgga cggcgagcag aagccgttcg cgcaggccga gctgcagctg cagagctttc   780
ccaccgtgct cctgttcccg ggccgcaccg ccaggcccat caagtacccg tcggagaaga   840
gggacgtcga ctcgctcctc gccttcgtca acagcctccg gtgagagacg acctccagtg   900
agcgagaacc atcgttctct gtcagtctgt atgatcttat gttggtcttt atgagtttat   960
ctaggttcgt agagaaggga ggtggagggg actgggtttg gtagtgacac aggaaggaac  1020
gagggttcag gggggaaaaa tcaggtgtag cttttgtaac tgcaaaatga ttgcagcatg  1080
tatacctgaa gtctgagctt ctgaggccct gtgcttggta gctgagggag aggttacttg  1140
tgtgtgctta tagtcagtgg cgagtgccta ctataaggtt caccggtcat ctaaagcact  1200
gttgtaaact gtatt                                                   1215
```

<210> SEQ ID NO 2
<211> LENGTH: 293
<212> TYPE: PRT
<213> ORGANISM: Zea mays
<220> FEATURE:
<221> NAME/KEY: UNSURE
<222> LOCATION: (91)
<223> OTHER INFORMATION: Xaa = any amino acid

<400> SEQUENCE: 2

```
Phe Pro Asp Ala Ser Glu Val Gln Glu Leu Val Arg Thr Lys Gly Leu
 1               5                  10                  15

Phe Ser Phe Tyr Glu Asp Gly His Gln Glu Cys Cys Arg Val Arg Lys
             20                  25                  30

Val Arg Pro Leu Arg Arg Ala Leu Lys Gly Leu Arg Ala Trp Ile Thr
         35                  40                  45

Gly Gln Arg Lys Asp Gln Ser Pro Gly Thr Arg Ala Ser Ile Pro Ile
     50                  55                  60

Val Gln Val Asp Pro Ser Phe Glu Gly Leu Asp Gly Gly Ala Gly Ser
 65                  70                  75                  80

Leu Val Lys Trp Asn Pro Val Ala Asn Val Xaa Gly Lys Asp Ile Trp
                 85                  90                  95

Thr Phe Leu Arg Thr Met Asp Val Pro Val Asn Thr Leu His Ala Gln
            100                 105                 110

Gly Tyr Val Ser Ile Gly Cys Glu Pro Cys Thr Arg Pro Val Leu Pro
        115                 120                 125

Gly Gln His Glu Arg Glu Gly Arg Trp Trp Trp Glu Asp Ala Lys Ala
    130                 135                 140

Lys Glu Cys Gly Leu His Lys Gly Asn Ile Asp Lys Asp Ala Gln Ala
145                 150                 155                 160

Ala Ala Pro Arg Ser Ala Asn Gly Asn Gly Ser Ala Gly Ala Pro Asp
                165                 170                 175

Ile Phe Glu Ser Pro Ala Val Val Ser Leu Thr Arg Thr Gly Ile Glu
            180                 185                 190

Asn Leu Leu Arg Leu Glu Asn Arg Ala Glu Pro Trp Leu Val Val Leu
        195                 200                 205

Tyr Ala Pro Trp Cys Pro Phe Cys Gln Ala Met Glu Ala Ser Tyr Val
    210                 215                 220

Glu Leu Ala Glu Lys Leu Ala Gly Ser Gly Val Lys Val Ala Lys Phe
225                 230                 235                 240

Arg Ala Asp Gly Glu Gln Lys Pro Phe Ala Gln Ala Glu Leu Gln Leu
                245                 250                 255
```

```
Gln Ser Phe Pro Thr Val Leu Leu Phe Pro Gly Arg Thr Ala Arg Pro
        260                 265                 270

Ile Lys Tyr Pro Ser Glu Lys Arg Asp Val Asp Ser Leu Leu Ala Phe
        275                 280                 285

Val Asn Ser Leu Arg
        290

<210> SEQ ID NO 3
<211> LENGTH: 1210
<212> TYPE: DNA
<213> ORGANISM: Impatiens balsamia

<400> SEQUENCE: 3
gcacgaggta catgttccct gatgcaattg tagtacaagg attagtaaga accaaaggac      60
tgttctcttt ctacgaagac ggacatcaag agtgctgccg cgtcagaaaa gtgaggccac     120
tgaggcgtgc tctcaagggt ctccgcgctt ggatcacggg gcaaagaaaa gaccagtcgc     180
cgggaacgag atcggagatc ccagtcgtcc aagtggatcc ctcttttgag ggattggttg     240
gtggagaggg tagcctggtg aagtggaatc cgctggctaa tgtagatggt cgtgatgtat     300
ggaatttcct ccgagctatg aatgtgcctg ttaatgcact tcatagccag ggttatgtct     360
cgattgggtg cgaaccgtgc acccgaccgg tgttacctgg gcaacatgag agagaaggca     420
ggtggtggtg ggaggatgct gcggctaagg agtgtggcct acataaagga aatataaagg     480
atgccaatgg gaatggggtt gctcaagctg agggaggaga aggaactgtt acggatgctg     540
atattttttga atccaagaat gtggtgacac tgagtagaag cgggattgag aatctgtcga     600
aacttcagga gaggaaagag ccatggatcg tggtcctgta tgcaccttgg tgccagttct     660
gccagggtat ggaaaaatca tacttggaat tggctgaaaa gctggcggtg agcggtggtg     720
gtgtgaaggt agggaaattc cgggcagatg gtgcagaaaa ggagtttgct caccaagaat     780
tgcagctggg gagcttttcca acaatactct tcttcccccaa acactcatct aaagccatca     840
agtacccatc tgagaaaagg gacgtggagt cattgttggc ttttgtgaac gcactcagat     900
gaatcaactg cagaaaccta gcagagctca actggattgt tgagttcata atgctttgac     960
gaatccaata aaacacccac ccgcccctgt tgtaagatgg tcagttagtc tctgttctgt    1020
tgtggcttgg tggccagagt tttggttacg taaaaggtag ctagcaactc agaagagtcc    1080
gttttggttt catttttcttc ttctttttttg tttgattgat ttggttaaca taaaagctat    1140
cagttgttta aaccaaaaaa aaaaaaaaaa aaaaaaaaaa aaaaaaaaaa aaaaaaaaaa    1200
aaaaaaaaaa                                                           1210

<210> SEQ ID NO 4
<211> LENGTH: 299
<212> TYPE: PRT
<213> ORGANISM: Impatiens balsamia

<400> SEQUENCE: 4

Thr Arg Tyr Met Phe Pro Asp Ala Ile Val Val Gln Gly Leu Val Arg
  1               5                  10                  15

Thr Lys Gly Leu Phe Ser Phe Tyr Glu Asp Gly His Gln Glu Cys Cys
             20                  25                  30

Arg Val Arg Lys Val Arg Pro Leu Arg Arg Ala Leu Lys Gly Leu Arg
         35                  40                  45

Ala Trp Ile Thr Gly Gln Arg Lys Asp Gln Ser Pro Gly Thr Arg Ser
     50                  55                  60
```

```
Glu Ile Pro Val Val Gln Val Asp Pro Ser Phe Glu Gly Leu Val Gly
 65                  70                  75                  80

Gly Glu Gly Ser Leu Val Lys Trp Asn Pro Leu Ala Asn Val Asp Gly
                 85                  90                  95

Arg Asp Val Trp Asn Phe Leu Arg Ala Met Asn Val Pro Val Asn Ala
            100                 105                 110

Leu His Ser Gln Gly Tyr Val Ser Ile Gly Cys Glu Pro Cys Thr Arg
        115                 120                 125

Pro Val Leu Pro Gly Gln His Glu Arg Glu Gly Arg Trp Trp Trp Glu
    130                 135                 140

Asp Ala Ala Lys Glu Cys Gly Leu His Lys Gly Asn Ile Lys Asp
145                 150                 155                 160

Ala Asn Gly Asn Gly Val Ala Gln Ala Glu Gly Gly Glu Gly Thr Val
                165                 170                 175

Thr Asp Ala Asp Ile Phe Glu Ser Lys Asn Val Val Thr Leu Ser Arg
            180                 185                 190

Ser Gly Ile Glu Asn Leu Ser Lys Leu Gln Glu Arg Lys Glu Pro Trp
        195                 200                 205

Ile Val Val Leu Tyr Ala Pro Trp Cys Gln Phe Cys Gln Gly Met Glu
    210                 215                 220

Lys Ser Tyr Leu Glu Leu Ala Glu Lys Leu Ala Val Ser Gly Gly Gly
225                 230                 235                 240

Val Lys Val Gly Lys Phe Arg Ala Asp Gly Ala Glu Lys Glu Phe Ala
                245                 250                 255

His Gln Glu Leu Gln Leu Gly Ser Phe Pro Thr Ile Leu Phe Phe Pro
            260                 265                 270

Lys His Ser Ser Lys Ala Ile Lys Tyr Pro Ser Glu Lys Arg Asp Val
        275                 280                 285

Glu Ser Leu Leu Ala Phe Val Asn Ala Leu Arg
    290                 295

<210> SEQ ID NO 5
<211> LENGTH: 1795
<212> TYPE: DNA
<213> ORGANISM: Glycine max

<400> SEQUENCE: 5
ttcggcacga gatctactct ctattttcct agcttagatt ccttctccaa tggctcttgc      60
cgtttccact acttcttcct cttcagctgc agcagcagca gcagcgtcga gctctttctt     120
ctcgcgcctt ggatcttcat cggacgctaa agctccgcaa attggttcct ttcggtttcc     180
ggagaggcct caagtttcgt ctggtgttgt taatttaact caaagacgct cctcggtgag     240
gccactcaat gccgaaccgc aacggaatga ttctgttgtt cctcttgcag caactatcgt     300
tgctcctgag gttgagaagg agaaagaaga ttttgagcaa ttagcgaaag accttgaaaa     360
ttcatctcct cttgagatta tggataaggc cctcgagaaa tttgggaacg acatcgctat     420
tgcctttagt ggtgctgaag atgttgcttt gattgagtat gcacatttga cgggtcgacc     480
ctacagagtg tttagtcttg acactgggag actgaaccca gaaacctaca atttttttga     540
cgctgttgag aagcattatg gaattcatat tgagtacatg ttccctgatg cggttgaggt     600
tcaggcatta gtaagaacta aggggctctt ctcattttac gaggatgggc atcaagagtg     660
ctgtagagta agaaaggtga ggcccttgag gagagccctt aagggtctca agcatggat      720 tactggacag agaaaagacc agtctcctgg tactaggtct gaaatcccta ttgtccaggt     780
```

-continued

```
tgatcctgtt tttgagggac tggatggtgg aattggcagc ctggtgaagt ggaacccggt      840
tgcaaatgtt aatggtctag acatatggaa cttccttagg accatgaatg ttcctgtaaa      900
ttcattgcat tcccaaggat atgtttcgat tggctgtgag ccatgcacaa ggccggtttt      960
acccggacaa catgaaagag aaggaaggtg gtggtgggag gatgccaaag ccaaggagtg     1020
tggtcttcac aaaggtaatt tgaaacagga gatgctgcc cagcttaatg gaaatgggac      1080
ctcccaagga aatggctctg ccactgttgc tgacattttc atctcccaga atgtggtcag     1140
cttgagcagg tccgggattg agaatttggc aaaattagag aaccgaaaag aacactggct     1200
tgttgtgctc tatgcaccat ggtgccgctt ctgtcaggct atggaggagt cgtatgttga     1260
tctggcagag aagttagcaa ggtcaggagt gaaggttgca aaattcagag ccgatggaga     1320
gcagaaggaa tatgcaaaga gtgaactgca gttgggaagc ttccccacaa tacttctctt     1380
ccccaagcac tcttctcaac caattaagta cccttcagaa agagagatg ttgattcatt      1440
gacggcattc gtgaatgcct acggtgatg gtcaattgag tatcttgctc aatgttccgt      1500
cgtaccatac cggcaataaa tttcttcaca gatttgggca attcactgaa atgggaatg      1560
gcagttttg atagcaaaac gaagattctc agctagcagt atccctgtat agatttagat      1620
aaccttcctc acaaatataa ttgtagtagt catgaggagg atgtgatttc ctgttttgtt     1680
agatgagtag agttatggtt gtattatgtt gtttcttcac tatcataatc tactttttta     1740
gattttgcca aaaaaaaaa aaaaaaaaa aaaaaaaaa aaaaaaaaa aaaaa              1795
```

<210> SEQ ID NO 6
<211> LENGTH: 472
<212> TYPE: PRT
<213> ORGANISM: Glycine max

<400> SEQUENCE: 6

```
Met Ala Leu Ala Val Ser Thr Thr Ser Ser Ser Ala Ala Ala
  1               5                  10                  15

Ala Ala Ala Ser Ser Ser Phe Phe Ser Arg Leu Gly Ser Ser Ser Asp
                 20                  25                  30

Ala Lys Ala Pro Gln Ile Gly Ser Phe Arg Phe Pro Glu Arg Pro Gln
             35                  40                  45

Val Ser Gly Val Val Asn Leu Thr Gln Arg Arg Ser Ser Val Arg
         50                  55                  60

Pro Leu Asn Ala Glu Pro Gln Arg Asn Asp Ser Val Val Pro Leu Ala
 65                  70                  75                  80

Ala Thr Ile Val Ala Pro Glu Val Glu Lys Glu Lys Glu Asp Phe Glu
                 85                  90                  95

Gln Leu Ala Lys Asp Leu Glu Asn Ser Ser Pro Leu Glu Ile Met Asp
            100                 105                 110

Lys Ala Leu Glu Lys Phe Gly Asn Asp Ile Ala Ile Ala Phe Ser Gly
        115                 120                 125

Ala Glu Asp Val Ala Leu Ile Glu Tyr Ala His Leu Thr Gly Arg Pro
    130                 135                 140

Tyr Arg Val Phe Ser Leu Asp Thr Gly Arg Leu Asn Pro Glu Thr Tyr
145                 150                 155                 160

Lys Phe Phe Asp Ala Val Glu Lys His Tyr Gly Ile His Ile Glu Tyr
                165                 170                 175

Met Phe Pro Asp Ala Val Glu Val Gln Ala Leu Val Arg Thr Lys Gly
            180                 185                 190

Leu Phe Ser Phe Tyr Glu Asp Gly His Gln Glu Cys Cys Arg Val Arg
```

```
                   195                 200                 205
Lys Val Arg Pro Leu Arg Arg Ala Leu Lys Gly Leu Lys Ala Trp Ile
    210                 215                 220

Thr Gly Gln Arg Lys Asp Gln Ser Pro Gly Thr Arg Ser Glu Ile Pro
225                 230                 235                 240

Ile Val Gln Val Asp Pro Val Phe Glu Gly Leu Asp Gly Ile Gly
                245                 250                 255

Ser Leu Val Lys Trp Asn Pro Val Ala Asn Val Asn Gly Leu Asp Ile
                260                 265                 270

Trp Asn Phe Leu Arg Thr Met Asn Val Pro Val Asn Ser Leu His Ser
            275                 280                 285

Gln Gly Tyr Val Ser Ile Gly Cys Glu Pro Cys Thr Arg Pro Val Leu
        290                 295                 300

Pro Gly Gln His Glu Arg Glu Gly Arg Trp Trp Trp Glu Asp Ala Lys
305                 310                 315                 320

Ala Lys Glu Cys Gly Leu His Lys Gly Asn Leu Lys Gln Glu Asp Ala
                325                 330                 335

Ala Gln Leu Asn Gly Asn Gly Thr Ser Gln Gly Asn Gly Ser Ala Thr
            340                 345                 350

Val Ala Asp Ile Phe Ile Ser Gln Asn Val Val Ser Leu Ser Arg Ser
        355                 360                 365

Gly Ile Glu Asn Leu Ala Lys Leu Glu Asn Arg Lys Glu His Trp Leu
    370                 375                 380

Val Val Leu Tyr Ala Pro Trp Cys Arg Phe Cys Gln Ala Met Glu Glu
385                 390                 395                 400

Ser Tyr Val Asp Leu Ala Glu Lys Leu Ala Arg Ser Gly Val Lys Val
                405                 410                 415

Ala Lys Phe Arg Ala Asp Gly Glu Gln Lys Glu Tyr Ala Lys Ser Glu
            420                 425                 430

Leu Gln Leu Gly Ser Phe Pro Thr Ile Leu Leu Phe Pro Lys His Ser
        435                 440                 445

Ser Gln Pro Ile Lys Tyr Pro Ser Glu Lys Arg Asp Val Asp Ser Leu
    450                 455                 460

Thr Ala Phe Val Asn Ala Leu Arg
465                 470

<210> SEQ ID NO 7
<211> LENGTH: 1629
<212> TYPE: DNA
<213> ORGANISM: Glycine max

<400> SEQUENCE: 7
gcacgaggag agaacccata acagctagtt aatggccctc gctttcactt cttcaatttc      60
cgcaccaact tccaccttcc catcatcgga acccaaactt ccgcaaattg ggtcaattag     120
gatttcggag aggcccattg gaggcgccgt taatttcaat ttatctcaaa gacggagctt     180
ggtaaagccc gttaacgccg aacctccacg caaggattcc attgttcctc tcgcagcaac     240
aaccatcgtt gcttctgctt ctgagacgaa agaggaagat tttgaacaga tagccagtga     300
tctcgacaat gcttcacctc ttgaaatcat ggatagagcc ctcgacaaat tcggcaacga     360
catagctatt gccttcagtg gtgctgaaga tgttgctttg attgagtatg cgaaattgac     420
gggtcgaccc tttagggttt tcagtttgga cactgggaga ctgaacccag aaacttatca     480 acttttgat gcggttgaga agcattatgg aattcgcatt gagtacatgt tccctgatgc     540
```

-continued

```
tgttgaggtt caggcattgg tgaggagtaa ggggttattc tctttctacg aggatgggca    600
ccaagagtgt tgcagggtga gaaaggtgag gcctttaagg agggccctta agggtctcag    660
agcatggata actggtcaga ggaaagacca gtcacctggt actaggtctg aaataccggt    720
tgttcaggtt gatccggctt tgagggaat ggatggtgga attggaagct tggtgaagtg     780
gaaccctgtt gcaaatgtga agggccatga catatggaac ttccttagga ccatgaatgt    840
gcctgtgaat tccttgcatg caaaaggata tgtttccatt gggtgtgagc cctgcactag    900
gcctgtttta cctgggcaac atgaaaggga agggaggtgg tggtgggagg atgccaaagc    960
taaggaatgt ggtcttcaca aaggaaatgt aaagcagcag aaagaggagg atgttaatgg    1020
aaatgggcta tcccaatccc atgcaaatgg tgatgctacc actgtgcctg acattttcaa    1080
cagcccgaat gtagttaact tgagcaggac tggaattgag aatttggcaa aattggagga    1140
ccgaaaggaa ccatggcttg ttgtgcttta tgcaccatgg tgcccctact gccaggctat    1200
ggaggaatct tatgttgact agcagacaa gttagcaggg tcaacaggga tgaaggttgg     1260
aaaatttaga gcagatggag aacagaaaga atttgcaaag agtgaactgc aattgggaag    1320
cttccctacg atattatttt tcccaaagca ttcgtctcgg ccaacaataa agtatccctc    1380
agaaaagaga gatgttgatt ccttgatggc atttgtaaat gccttaagat gaggatatca    1440
ggaaattttc ttcgtttttg ggttgcaatt ccactttgac tatacgtaca gcgggttcct    1500
tctttatgct attacgtgta tataccattc gtttacagat tcttctgtga actcgttgga    1560
agtgggaatg gaggtttata caaataagat actcagtttt gaatggtttt aaaaaaaaa     1620 aaaaaaaaa                                                            1629
```

<210> SEQ ID NO 8
<211> LENGTH: 466
<212> TYPE: PRT
<213> ORGANISM: Glycine max

<400> SEQUENCE: 8

```
Met Ala Leu Ala Phe Thr Ser Ser Ile Ser Ala Pro Thr Ser Thr Phe
  1               5                  10                  15

Pro Ser Ser Glu Pro Lys Leu Pro Gln Ile Gly Ser Ile Arg Ile Ser
             20                  25                  30

Glu Arg Pro Ile Gly Gly Ala Val Asn Phe Asn Leu Ser Gln Arg Arg
         35                  40                  45

Ser Leu Val Lys Pro Val Asn Ala Glu Pro Pro Arg Lys Asp Ser Ile
     50                  55                  60

Val Pro Leu Ala Ala Thr Thr Ile Val Ala Ser Ala Ser Glu Thr Lys
 65                  70                  75                  80

Glu Glu Asp Phe Glu Gln Ile Ala Ser Asp Leu Asp Asn Ala Ser Pro
                 85                  90                  95

Leu Glu Ile Met Asp Arg Ala Leu Asp Lys Phe Gly Asn Asp Ile Ala
            100                 105                 110

Ile Ala Phe Ser Gly Ala Glu Asp Val Ala Leu Ile Glu Tyr Ala Lys
        115                 120                 125

Leu Thr Gly Arg Pro Phe Arg Val Phe Ser Leu Asp Thr Gly Arg Leu
    130                 135                 140

Asn Pro Glu Thr Tyr Gln Leu Phe Asp Ala Val Glu Lys His Tyr Gly
145                 150                 155                 160

Ile Arg Ile Glu Tyr Met Phe Pro Asp Ala Val Glu Val Gln Ala Leu
                165                 170                 175
```

-continued

Val Arg Ser Lys Gly Leu Phe Ser Phe Tyr Glu Asp Gly His Gln Glu
                180                 185                 190

Cys Cys Arg Val Arg Lys Val Arg Pro Leu Arg Arg Ala Leu Lys Gly
            195                 200                 205

Leu Arg Ala Trp Ile Thr Gly Gln Arg Lys Asp Gln Ser Pro Gly Thr
    210                 215                 220

Arg Ser Glu Ile Pro Val Val Gln Val Asp Pro Ala Phe Glu Gly Met
225                 230                 235                 240

Asp Gly Gly Ile Gly Ser Leu Val Lys Trp Asn Pro Val Ala Asn Val
                245                 250                 255

Lys Gly His Asp Ile Trp Asn Phe Leu Arg Thr Met Asn Val Pro Val
            260                 265                 270

Asn Ser Leu His Ala Lys Gly Tyr Val Ser Ile Gly Cys Glu Pro Cys
        275                 280                 285

Thr Arg Pro Val Leu Pro Gly Gln His Glu Arg Glu Gly Arg Trp Trp
    290                 295                 300

Trp Glu Asp Ala Lys Ala Lys Glu Cys Gly Leu His Lys Gly Asn Val
305                 310                 315                 320

Lys Gln Gln Lys Glu Glu Asp Val Asn Gly Asn Gly Leu Ser Gln Ser
                325                 330                 335

His Ala Asn Gly Asp Ala Thr Thr Val Pro Asp Ile Phe Asn Ser Pro
            340                 345                 350

Asn Val Val Asn Leu Ser Arg Thr Gly Ile Glu Asn Leu Ala Lys Leu
        355                 360                 365

Glu Asp Arg Lys Glu Pro Trp Leu Val Val Leu Tyr Ala Pro Trp Cys
    370                 375                 380

Pro Tyr Cys Gln Ala Met Glu Glu Ser Tyr Val Asp Leu Ala Asp Lys
385                 390                 395                 400

Leu Ala Gly Ser Thr Gly Met Lys Val Gly Lys Phe Arg Ala Asp Gly
                405                 410                 415

Glu Gln Lys Glu Phe Ala Lys Ser Glu Leu Gln Leu Gly Ser Phe Pro
            420                 425                 430

Thr Ile Leu Phe Phe Pro Lys His Ser Ser Arg Pro Thr Ile Lys Tyr
    435                 440                 445

Pro Ser Glu Lys Arg Asp Val Asp Ser Leu Met Ala Phe Val Asn Ala
450                 455                 460

Leu Arg
465

<210> SEQ ID NO 9
<211> LENGTH: 1827
<212> TYPE: DNA
<213> ORGANISM: Triticum aestivum

<400> SEQUENCE: 9
gcacgaggtt aaaacacatt tgccagctcc gacaaacatc cctgcgaatt tgagagggag    60
gaagggttca ttcagcggcc ggtaatcaat ggcttccgct actgcttcca tctcgtcgca   120
ctccatcgcc ctgcgcgatc tcaaagccgc gaggattgga gccgtgaggc agcaggtggc   180
cgtggttcct gcgggcctgc cggcaacggc gcccaaggc cagcgcgcga gggcggtgcg   240
cccgctgtgc gcggcggagc cagcgaggaa gccagtgtcg gcctccgcgg cctcgtcgcc   300
ggtggcgccg gtggaggagg aggcatctgc cgtggcggcc gtggactacg aggccctggc   360
gcaggagctg gtgggcgcgt cgccgctgga gatcatggat cgtgcgctcg acatgttcgg   420

-continued

```
ctccgaaatc gccatcgcct tcagtggtgc cgaggacgtg gccctcatcg aatacgcgaa      480
actgactgga cgcccttca gggtgttcag ccttgacact gggcgactga acccagagac      540
atacgaactc ttcgacaagg tggagaagca ctatggtatc cacatcgagt acatgttccc      600
tgaggccagc gaggtgcaag accttgtgag gagcaagggc ctcttctctt tctacgagga      660
cggacaccag gagtgctgca gggtgaggaa ggttcggccc ttgaggaggg ccctcaaggg      720
cctcaaggcc tggatcaccg ggcagaggaa ggatcagtcc cctggcacca gagccagcat      780
ccctgttgtt caagttgatc cgtcttttga agggctggat ggtggagccg gtagcttgat      840
caagtggaac cctgtggcta atgtggatgg caaggatatc tggaccttcc tcaggaccat      900
ggatgtccct gtgaacaccc tgcatgctca aggctacgtc tccattgggt gcgagccgtg      960
caccaggccc gtgttgccgg ggcagcacga gagggaaggg aggtggtggt gggaggacgc     1020
cacggccaag gagtgcggcc tgcacaacgg taacatcgac aaggaaggtc aggcacccaa     1080
ggtcggcgtc aacggcaacg gctcggccga ggccagcgcc ccagacatct tccagagcca     1140
ggccatcgtc aacctcaccc gtcccgggat cgagaacctc ctgcggctcg agaaccgcgc     1200
cgagccgtgg ctcaccgtcc tctacgctcc ctggtgccca tactgccagg caatggaggc     1260
gtcctacgtt gagctggccg agaagctgag cggctcaggc atcaaggtgg ccaagttccg     1320
cgcggacggc gagcagaagc cattcgcgca ggcggagctg caactacaga gcttcccgac     1380
gatcctcctg ttccccggcc gcaccgtgaa gcccatcaag tacccgtccg agaagaggga     1440
cgtccagtcc ctcctcgcct tcgtgaacag cctcagatga gtggtcagag aaccggagaa     1500
ccatcgttct ctgcattggt accggcggtg tctaggcatt attatgtagt ggtagcgaga     1560
gaggatggat caacggaaat gttggagaca gaggagtgtg gggacgcagg gacagcggct     1620
caaagcccct ccattataag ggggtgggga tttgtgtgta gttgtagcta gatgtttgta     1680
aggaagttca aataagagta ctagttttga aattttgatc caaggcttca tcgagagttt     1740
ggacaatata ctcgtggttc actcggtcaa aaaaaaaaaa aaaaaaaaaa aaaaaaaaaa     1800
aaaaaaaaaa aaaaaaaaaa aaaaaaa                                         1827
```

<210> SEQ ID NO 10
<211> LENGTH: 463
<212> TYPE: PRT
<213> ORGANISM: Triticum aestivum

<400> SEQUENCE: 10

```
Met Ala Ser Ala Thr Ala Ser Ile Ser Ser His Ser Ile Ala Leu Arg
 1               5                  10                  15

Asp Leu Lys Ala Ala Arg Ile Gly Ala Val Arg Gln Gln Val Ala Val
            20                  25                  30

Val Pro Ala Gly Leu Pro Ala Thr Ala Pro Lys Gly Gln Arg Ala Arg
         35                  40                  45

Ala Val Arg Pro Leu Cys Ala Ala Glu Pro Ala Lys Pro Val Ser
     50                  55                  60

Ala Ser Ala Ala Ser Pro Val Ala Pro Val Glu Glu Glu Ala Ser
 65                  70                  75                  80

Ala Val Ala Ala Val Asp Tyr Glu Ala Leu Ala Gln Glu Leu Val Gly
            85                  90                  95

Ala Ser Pro Leu Glu Ile Met Asp Arg Ala Leu Asp Met Phe Gly Ser
        100                 105                 110

Glu Ile Ala Ile Ala Phe Ser Gly Ala Glu Asp Val Ala Leu Ile Glu
    115                 120                 125
```

```
Tyr Ala Lys Leu Thr Gly Arg Pro Phe Arg Val Phe Ser Leu Asp Thr
    130                 135                 140
Gly Arg Leu Asn Pro Glu Thr Tyr Glu Leu Phe Asp Lys Val Glu Lys
145                 150                 155                 160
His Tyr Gly Ile His Ile Glu Tyr Met Phe Pro Glu Ala Ser Glu Val
                165                 170                 175
Gln Asp Leu Val Arg Ser Lys Gly Leu Phe Ser Phe Tyr Glu Asp Gly
            180                 185                 190
His Gln Glu Cys Cys Arg Val Arg Lys Val Arg Pro Leu Arg Arg Ala
        195                 200                 205
Leu Lys Gly Leu Lys Ala Trp Ile Thr Gly Gln Arg Lys Asp Gln Ser
    210                 215                 220
Pro Gly Thr Arg Ala Ser Ile Pro Val Val Gln Val Asp Pro Ser Phe
225                 230                 235                 240
Glu Gly Leu Asp Gly Gly Ala Gly Ser Leu Ile Lys Trp Asn Pro Val
                245                 250                 255
Ala Asn Val Asp Gly Lys Asp Ile Trp Thr Phe Leu Arg Thr Met Asp
            260                 265                 270
Val Pro Val Asn Thr Leu His Ala Gln Gly Tyr Val Ser Ile Gly Cys
        275                 280                 285
Glu Pro Cys Thr Arg Pro Val Leu Pro Gly Gln His Glu Arg Glu Gly
    290                 295                 300
Arg Trp Trp Trp Glu Asp Ala Thr Ala Lys Glu Cys Gly Leu His Asn
305                 310                 315                 320
Gly Asn Ile Asp Lys Glu Gly Gln Ala Pro Lys Val Gly Val Asn Gly
                325                 330                 335
Asn Gly Ser Ala Glu Ala Ser Ala Pro Asp Ile Phe Gln Ser Gln Ala
            340                 345                 350
Ile Val Asn Leu Thr Arg Pro Gly Ile Glu Asn Leu Leu Arg Leu Glu
        355                 360                 365
Asn Arg Ala Glu Pro Trp Leu Thr Val Leu Tyr Ala Pro Trp Cys Pro
    370                 375                 380
Tyr Cys Gln Ala Met Glu Ala Ser Tyr Val Glu Leu Ala Glu Lys Leu
385                 390                 395                 400
Ser Gly Ser Gly Ile Lys Val Ala Lys Phe Arg Ala Asp Gly Glu Gln
                405                 410                 415
Lys Pro Phe Ala Gln Ala Glu Leu Gln Leu Gln Ser Phe Pro Thr Ile
            420                 425                 430
Leu Leu Phe Pro Gly Arg Thr Val Lys Pro Ile Lys Tyr Pro Ser Glu
        435                 440                 445
Lys Arg Asp Val Gln Ser Leu Leu Ala Phe Val Asn Ser Leu Arg
    450                 455                 460

<210> SEQ ID NO 11
<211> LENGTH: 463
<212> TYPE: PRT
<213> ORGANISM: Catharanthus roseus

<400> SEQUENCE: 11

Met Ala Leu Ala Phe Thr Ser Ser Thr Ala Ile His Gly Ser Leu Ser
  1               5                  10                  15

Ser Ser Phe Glu Gln Thr Lys Ala Ala Ala Gln Phe Gly Ser Phe
            20                  25                  30

Gln Pro Leu Asp Arg Pro His Thr Ile Ser Pro Ser Val Asn Val Ser
```

-continued

```
            35                  40                  45
Arg Arg Arg Leu Ala Val Lys Pro Ile Asn Ala Glu Pro Lys Arg Asn
             50                  55                  60

Glu Ser Ile Val Pro Ser Ala Ala Thr Thr Val Ala Pro Glu Val Glu
 65                  70                  75                  80

Glu Lys Val Asp Val Glu Asp Tyr Glu Lys Leu Ala Asp Glu Leu Gln
                 85                  90                  95

Asn Ala Ser Pro Leu Glu Ile Met Asp Lys Ser Leu Ala Lys Phe Gly
                100                 105                 110

Asn Asp Ile Ala Ile Ala Phe Ser Gly Ala Glu Asp Val Ala Leu Ile
                115                 120                 125

Glu Tyr Ala His Leu Thr Gly Arg Pro Phe Arg Val Phe Ser Leu Asp
    130                 135                 140

Thr Gly Arg Leu Asn Pro Glu Thr Tyr Lys Phe Phe Asp Thr Val Glu
145                 150                 155                 160

Lys Gln Tyr Gly Ile His Ile Glu Tyr Met Phe Pro Asp Ala Val Glu
                165                 170                 175

Val Gln Ala Leu Val Arg Ser Lys Gly Leu Phe Ser Phe Tyr Glu Asp
                180                 185                 190

Gly His Gln Glu Cys Cys Arg Val Arg Lys Val Arg Pro Leu Arg Arg
                195                 200                 205

Ala Leu Lys Gly Leu Arg Ala Trp Ile Thr Gly Gln Arg Lys Asp Gln
    210                 215                 220

Ser Pro Gly Thr Arg Ser Glu Ile Pro Val Val Gln Val Asp Pro Val
225                 230                 235                 240

Phe Glu Gly Met Asp Gly Gly Val Gly Ser Leu Val Lys Trp Asn Pro
                245                 250                 255

Val Ala Asn Val Glu Gly Lys Asp Ile Trp Asn Phe Leu Arg Ala Met
                260                 265                 270

Asp Val Pro Val Asn Thr Leu His Ser Gln Gly Tyr Val Ser Ile Gly
                275                 280                 285

Cys Glu Pro Cys Thr Arg Pro Val Leu Pro Gly Gln His Glu Arg Glu
    290                 295                 300

Gly Arg Trp Cys Trp Glu Asp Ala Lys Ala Lys Glu Cys Gly Leu His
305                 310                 315                 320

Lys Gly Asp Ile Lys Glu Gly Thr Leu Ile Ile Trp Asp Gly Ala Val
                325                 330                 335

Asn Gly Asn Gly Ser Asp Thr Ile Ala Asp Ile Phe Asp Thr Asn Asn
                340                 345                 350

Val Thr Ser Leu Ser Arg Pro Gly Ile Glu Asn Leu Leu Lys Leu Glu
                355                 360                 365

Glu Arg Arg Glu Ala Trp Leu Val Leu Tyr Ala Pro Trp Cys Arg
    370                 375                 380

Phe Cys Gln Ala Met Glu Gly Ser Tyr Leu Glu Leu Ala Glu Lys Leu
385                 390                 395                 400

Ala Gly Ser Gly Val Lys Val Gly Lys Phe Lys Ala Asp Gly Asp Gln
                405                 410                 415

Lys Ala Phe Ala Gln Gln Glu Leu Gln Leu Asn Ser Ser Pro Thr Ile
                420                 425                 430

Leu Phe Phe Pro Lys His Ser Ser Lys Pro Ile Lys Tyr Pro Ser Glu
                435                 440                 445

Lys Arg Asp Val Asp Ser Leu Met Ala Phe Val Asn Ala Leu Arg
450                 455                 460
```

<210> SEQ ID NO 12
<211> LENGTH: 465
<212> TYPE: PRT
<213> ORGANISM: Arabidopsis thaliana

<400> SEQUENCE: 12

Met Ala Met Ser Val Asn Val Ser Ser Ser Ser Ser Gly Ile Ile
1               5                   10                  15

Asn Ser Arg Phe Gly Val Ser Leu Glu Pro Lys Val Ser Gln Ile Gly
            20                  25                  30

Ser Leu Arg Leu Leu Asp Arg Val His Val Ala Pro Val Ser Leu Asn
            35                  40                  45

Leu Ser Gly Lys Arg Ser Ser Val Lys Pro Leu Asn Ala Glu Pro
        50                  55                  60

Lys Thr Lys Asp Ser Met Ile Pro Leu Ala Ala Thr Met Val Ala Glu
65                  70                  75                  80

Ile Ala Glu Glu Val Glu Val Val Glu Ile Glu Asp Phe Glu Glu Leu
                85                  90                  95

Ala Lys Lys Leu Glu Asn Ala Ser Pro Leu Glu Ile Met Asp Lys Ala
            100                 105                 110

Leu Glu Lys Tyr Gly Asn Asp Ile Ala Ile Ala Phe Ser Gly Ala Glu
        115                 120                 125

Asp Val Ala Leu Ile Glu Tyr Ala His Leu Thr Gly Arg Pro Phe Arg
130                 135                 140

Val Phe Ser Leu Asp Thr Gly Arg Leu Asn Pro Glu Thr Tyr Arg Phe
145                 150                 155                 160

Phe Asp Ala Val Glu Lys His Tyr Gly Ile Arg Ile Glu Tyr Met Phe
                165                 170                 175

Pro Asp Ser Val Glu Val Gln Gly Leu Val Arg Ser Lys Gly Leu Phe
            180                 185                 190

Ser Phe Tyr Glu Asp Gly His Gln Glu Cys Cys Arg Val Arg Lys Val
        195                 200                 205

Arg Pro Leu Arg Arg Ala Leu Lys Gly Leu Lys Ala Trp Ile Thr Gly
210                 215                 220

Gln Arg Lys Asp Gln Ser Pro Gly Thr Arg Ser Glu Ile Pro Val Val
225                 230                 235                 240

Gln Val Asp Pro Val Phe Glu Gly Leu Asp Gly Val Gly Ser Leu
                245                 250                 255

Val Lys Trp Asn Pro Val Ala Asn Val Glu Gly Asn Asp Val Trp Asn
            260                 265                 270

Phe Leu Arg Thr Met Asp Val Pro Val Asn Thr Leu His Ala Ala Gly
        275                 280                 285

Tyr Ile Ser Ile Gly Cys Glu Pro Cys Thr Lys Ala Val Leu Pro Gly
290                 295                 300

Gln His Glu Arg Glu Gly Arg Trp Trp Trp Glu Asp Ala Lys Ala Lys
305                 310                 315                 320

Glu Cys Gly Leu His Lys Gly Asn Val Lys Glu Asn Ser Asp Asp Ala
                325                 330                 335

Lys Val Asn Gly Glu Ser Lys Ser Ala Val Ala Asp Ile Phe Lys Ser
            340                 345                 350

Glu Asn Leu Val Thr Leu Ser Arg Gln Gly Ile Glu Asn Leu Met Lys
        355                 360                 365

Leu Glu Asn Arg Lys Glu Pro Trp Ile Val Val Leu Tyr Ala Pro Trp

-continued

```
                 370                      375                      380
Cys Pro Phe Cys Gln Ala Met Glu Ala Ser Tyr Asp Glu Leu Ala Asp
385                 390                 395                 400

Lys Leu Ala Gly Ser Gly Ile Lys Val Ala Lys Phe Arg Ala Asp Gly
                405                 410                 415

Asp Gln Lys Glu Phe Ala Lys Gln Glu Leu Gln Leu Gly Ser Phe Pro
            420                 425                 430

Thr Ile Leu Val Phe Pro Lys Asn Ser Ser Arg Pro Ile Lys Tyr Pro
        435                 440                 445

Ser Glu Lys Arg Asp Val Glu Ser Leu Thr Ser Phe Leu Asn Leu Val
    450                 455                 460

Arg
465
```